United States Patent
Shiramizu

(10) Patent No.: US 7,348,188 B2
(45) Date of Patent: Mar. 25, 2008

(54) METHOD FOR ANALYZING METAL ELEMENT ON SURFACE OF WAFER

(75) Inventor: Yoshimi Shiramizu, Kawasaki (JP)

(73) Assignee: NEC Electronics Corporation, Kanagawa (JP)

( * ) Notice: Subject to any disclaimer, the term of this patent is extended or adjusted under 35 U.S.C. 154(b) by 386 days.

(21) Appl. No.: 11/070,096

(22) Filed: Mar. 3, 2005

(65) Prior Publication Data
US 2005/0196881 A1 Sep. 8, 2005

(30) Foreign Application Priority Data
Mar. 3, 2004 (JP) ............... 2004-059392

(51) Int. Cl.
*H01L 21/00* (2006.01)
(52) U.S. Cl. .................. 438/14; 438/476; 134/13; 134/10
(58) Field of Classification Search ............ 438/14, 438/476; 134/13, 10
See application file for complete search history.

(56) References Cited

U.S. PATENT DOCUMENTS

| | | | | |
|---|---|---|---|---|
| 5,527,707 | A * | 6/1996 | Fukazawa | 436/72 |
| 5,636,256 | A * | 6/1997 | Matumura et al. | 378/45 |
| 5,916,819 | A * | 6/1999 | Skrovan et al. | 438/692 |
| 5,972,726 | A * | 10/1999 | Saitoh et al. | 438/14 |
| 6,174,740 | B1 * | 1/2001 | Ohta et al. | 438/14 |
| 6,911,096 | B2 * | 6/2005 | Watanabe | 134/10 |
| 2002/0134406 | A1 * | 9/2002 | Heo et al. | 134/3 |
| 2003/0084926 | A1 * | 5/2003 | Watanabe | 134/33 |
| 2005/0048659 | A1 * | 3/2005 | Shiramizu | 436/72 |
| 2005/0196881 | A1 * | 9/2005 | Shiramizu | 438/14 |

FOREIGN PATENT DOCUMENTS

| | | |
|---|---|---|
| DE | 19713090 | 11/1997 |
| DE | 102004041410 | 5/2005 |
| JP | 02-028533 | 1/1990 |

(Continued)

OTHER PUBLICATIONS

Boubekeur, Hocine. (2002). Contamination Aspects in Integrating High Dielectric Constant and Ferroelectric Materials onto CMOS Processes. Universität Erlangen-Nürnberg, p. 20-23☐☐☐☐.*

(Continued)

*Primary Examiner*—Laura M. Schillinger
(74) *Attorney, Agent, or Firm*—Young & Thompson

(57) ABSTRACT

Various kinds of metal elements existing on the surface of a wafer are analyzed with higher sensitivity. A high concentration HF solution is dropped onto a surface of a wafer. By providing the droplets of high concentration HF solution, the native oxide film on the surface of the wafer is dissolved into the solution, and the metal elements or compounds thereof existing in vicinity of the surface of the wafer are eliminated from the wafer and are incorporated into the high concentration HF solution. The droplets formed by agglomerating the high concentration HF solution are aggregated at a predetermined position on the surface of the wafer. Then, the recovered droplet of the high concentration HF solution is dried. The aggregated material is irradiated with X-ray at an angle for promoting total reflection, and the total reflection X-ray fluorescence spectrometry is conducted to detect the emitted X-ray.

15 Claims, 7 Drawing Sheets

FOREIGN PATENT DOCUMENTS

| | | |
|---|---|---|
| JP | 10307087 A | 11/1998 |
| JP | 2001153768 A | 6/2001 |
| JP | 2004-028787 | 1/2004 |

OTHER PUBLICATIONS

Yamagami et al. (1999). VPD/TXRF Analysis of Trace Elements on a Silicon Wafer. X-Ray Spectrometry, vol. 28, p. 451-452.*

English translation of German Official Action regarding corresponding German application No. 10 2005 008 068.5-52, dated Sep. 28, 2006.

* cited by examiner

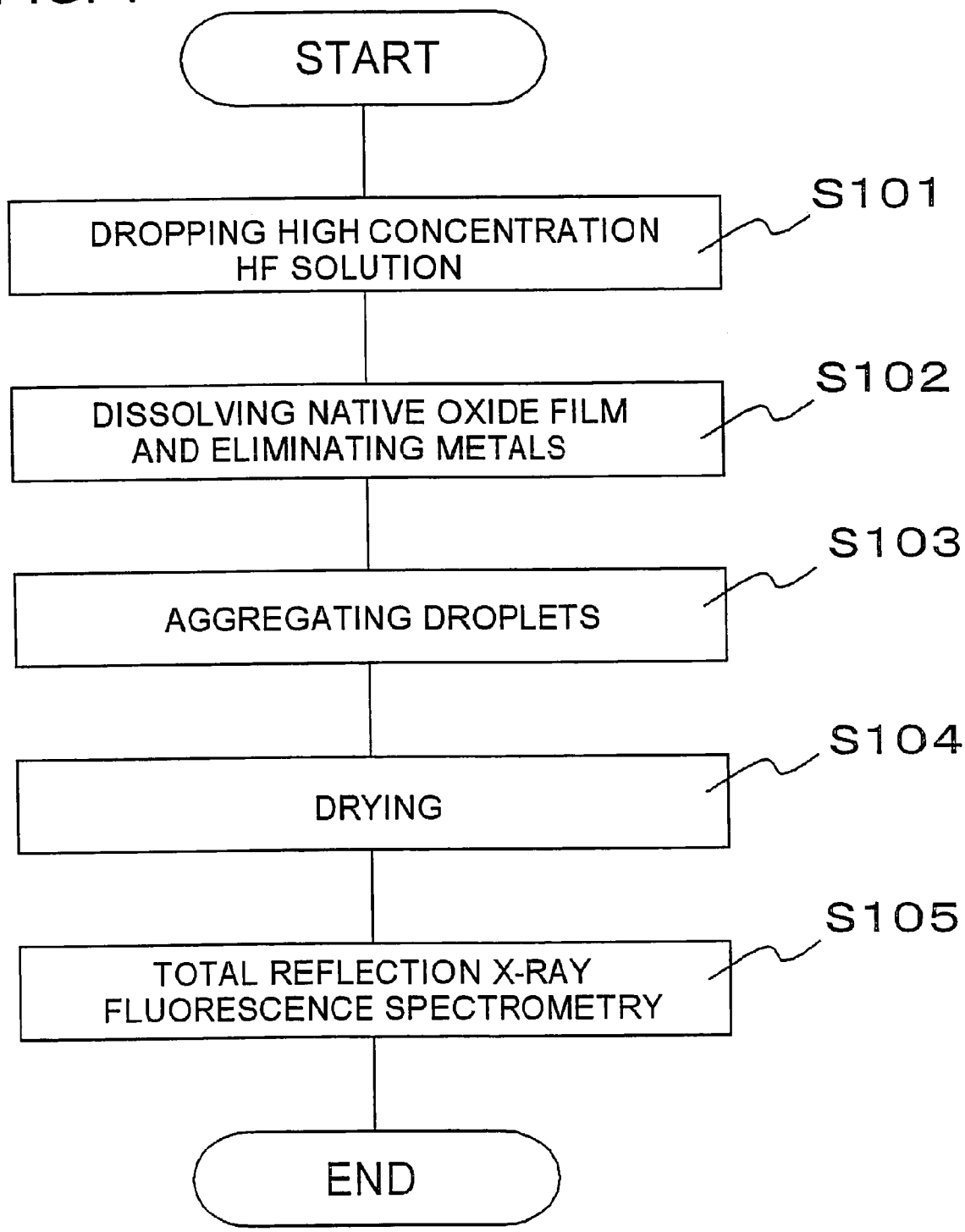

METHOD FOR ANALYZING METAL ELEMENT ON SURFACE OF WAFER

The present application is based on Japanese Patent Application NO. 2004-059392, the content of which is incorporated hereinto by reference.

BACKGROUND OF THE INVENTION

1. Field of the Invention

The present invention relates to a method for analyzing a metal element on a surface of a wafer.

2. Related Art

In recent years, while needs for achieving the increased integration of the semiconductor devices are growing, miniaturization of devices is increasing. On the other hand, required level for the cleanliness in semiconductor manufacturing process tends to become severer and severer. Control of the cleanliness on the surface of semiconductor substrate is a critical issue that influences a production yield of the products. In particular, since a metal impurity remaining thereon may possibly deteriorates electric characteristics of the devices, extremely high cleanliness is required. Analysis technique for precisely detecting and quantifying an impurity on a wafer surface is first required in order to reduce the amount of the impurity. In addition, a process for employing a high-k material for a gate insulating film or a capacitance film of a capacitor recently becomes to be adopted. In addition, metal elements such as ruthenium (Ru) and the like become to be employed as an electrode material. The utilization of new materials provides diversification of metal elements as the evaluation targets. Thus, methods for detecting the various metal elements with higher sensitivity are demanded.

The method for analyzing metal element on wafer surface generally includes a method for chemically analyzing thereof by dissolving a native oxide film generated on the surface with hydrofluoric acid vapor or the like to recover the existing contamination metal included on the surface or in the interior of the native oxide film and analyzing the metal including the recovered solution by atomic absorption spectrometry (AAS), inductively coupled plasma quadrupole mass spectrometry (ICPQMS) or the like. Japanese Patent Laid-Open No. 1990-28,533 discloses a technique, in which metal elements on the wafer surface are dissolved into a solution containing about 0.5 to 2 wt % of HF and the dissolved elements are recovered, and the recovered elements are analyzed by a chemically analyzing method.

The methods for analyzing the local contamination on the surface of the device includes a physically analyzing method for analyzing thereof by total reflection X-ray fluorescence spectrometry (TXRF), secondary ion mass spectrometry (SIMS) or the like. Japanese Patent Laid-Open No. 2004-28,787 discloses a technique for analyzing a metal element on a surface of a wafer by TXRF. According to Japanese Patent Laid-Open No. 2004-28,787, TXRF is a method for detecting fluorescent X-ray emitted from a measurement surface of an object when excited X-ray having better natural collimation is incident upon the measurement surface of the object at a lower incident angle equal to or less than a critical angle that is determined by a wave length thereof and kind of element. In Japanese Patent Laid-Open No. 2004-28,787, an etching vapor, which is generated by heating an etching solution, is in contact with a surface of a silicon wafer to form liquid droplets of the etchant solution containing the metal contaminants. Then, the liquid droplets are dried at their original positions to form residues having fine particle shapes. Then, X-ray is irradiated upon the silicon wafer, and fluorescent X-ray from the residues can be analyzed with information of their position by the total reflection X-ray fluorescence spectrometry.

SUMMARY OF THE INVENTION

However, the present inventors have investigated the above-described related art documents and have discovered that there is a room for further improving thereof in the following points.

First, elements such as Fe, In, Ti or the like cause interferences during a measurement by ICPQMS, and thus it is difficult to simultaneously analyze these elements with higher sensitivity, or analyze each of these elements at the same analysis condition. Further, sufficient sensitivity can not generally be obtained in TXRF or atomic absorption spectroscopy.

Second, among heavy metals, analysis for elements such as Ce the like, platinum group metal elements such as Ru, Pt, Ir and the like, and metal elements for forming high-k material such as Zr, Hf, Y, La and the like are difficult in general. The present inventors have investigated the possible causes thereof, and found that elements such as Ce react with high concentration hydrofluoric acid to generate insoluble materials in general. Further, it has been also found that elements such as platinum group metal elements and Zr, Hf, Y, La and the like are difficult to be eliminated from the silicon wafer since these elements cause mutual actions with the silicon wafer. Thus, it has been difficult to analyze these elements by methods that require dissolving these metal elements into liquid as described in Japanese Patent Laid-Open No. 1990-28,533. Further, concerning the disclosure of Japanese Patent Laid-Open No. 2004-28,787, since the analysis is conducted without moving the positions of the objects containing these metal elements on the wafer, sufficient sensitivity is not provided when elements existing in the objects are in a trace amount.

According to the present invention, there is provided a method for analyzing a metal element, comprising: dropping a liquid on a surface of a semiconductor wafer having an oxide film formed thereon to dissolve the oxide film in the liquid, thereby incorporating a metal element contained in the semiconductor wafer into the liquid, the liquid containing hydrofluoric acid at a concentration of equal to or greater than 20 wt %; aggregating the liquid containing the metal element on the semiconductor wafer; drying the liquid in the aggregating the liquid to obtain an aggregated material containing the metal element on the semiconductor wafer; and analyzing the metal element by detecting fluorescent X-ray emitted from the semiconductor wafer, the fluorescent X-ray being emitted by irradiating X-ray upon the semiconductor wafer at an incident angle of providing a total reflection thereof.

According to the present invention, the oxide film is dissolved by using a liquid containing hydrofluoric acid at high concentration of equal to or greater than 20 wt % and simultaneously to definitely incorporate the metal element contained in the wafer into the liquid. Thus, the present invention is advantageous over the technology disclosed in Japanese Patent Laid-Open No. 1990-28,533, in terms of definitely moving the metal element into the liquid to incorporate the metal element therein. Further, since the present invention includes conducting the analysis of the metal element by the total reflection X-ray fluorescence spectrometry, the metal element is not necessary to be dissolved into the liquid, unlike the above-described technology disclosed in Japanese Patent Laid-Open No. 1990-28,533, and it is sufficient that the metal element is just incorporated in the liquid. Thus, metal elements such as heavy metal elements, which are difficult to be analyzed in the conventional chemical analysises, can definitely be analyzed.

In addition, since the present invention includes aggregating the liquids containing the metal element on the semiconductor wafer, the metal elements on the surface of the wafer can be incorporated in the liquid and then, definitely be aggregated. The metal elements can be concentrated on the wafer to be utilized for the samples of the total reflection X-ray fluorescence spectrometry without further processing. Thus, unlike the technology disclosed in above-described Japanese Patent Laid-Open No. 2004-28,787 that includes analyzing without moving the metal elements on the wafer, a trace amount of the metal elements can be analyzed with higher sensitivity by a simple and easy technique.

Here, the surface of the wafer of this aspect of the present invention may include the metal elements or the like contained in or on the oxide film such as a native oxide film and the like formed on the surface of the wafer. Further, analyzing the metal elements according to the present invention may include analyzing a kind of the metal element. Further, analyzing the metal elements according to the present invention may also include analyzing a concentration of the metal element. In addition, analyzing the metal elements according to the present invention may also include analyzing a kind and a concentration of the metal element.

According to the present invention, there is provided a technology for analyzing various kinds of metal elements existing on the surface of the wafer at higher sensitivity by: dropping a liquid solution containing hydrofluoric acid at higher concentration onto a surface of a semiconductor wafer having an oxide film formed thereon to dissolve the oxide film into the liquid, thereby incorporating metal elements contained in the semiconductor wafer into the liquid; aggregating the liquid droplets containing the metal element on the semiconductor wafer; and drying the aggregated liquid droplets to obtain aggregated materials containing the metal elements on the semiconductor wafer.

BRIEF DESCRIPTION OF THE DRAWINGS

The above and other objects, advantages and features of the present invention will be more apparent from the following description taken in conjunction with the accompanying drawings, in which:

FIG. 1 is a flow chart, describing a procedure for analyzing a metal element on a wafer according to an embodiment;

DETAILED DESCRIPTION OF THE INVENTION

Figure 2A:
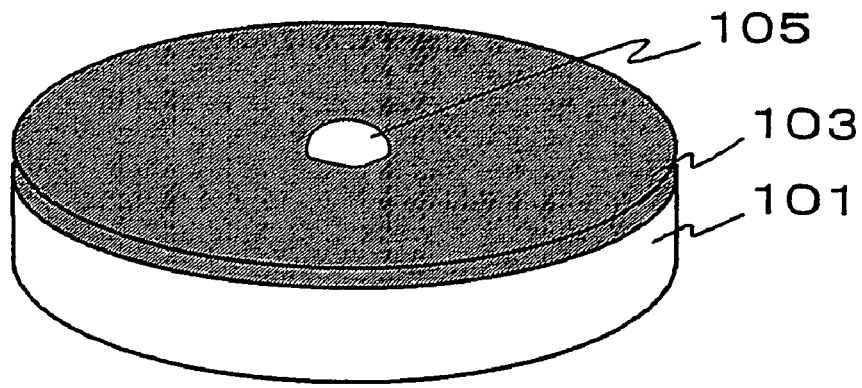
FIG. 2A is a schematic perspective view of a wafer, illustrating a procedure for analyzing the metal element on the wafer according to the embodiment.

The invention will be now described herein with reference to illustrative embodiments. Those skilled in the art will recognize that many alternative embodiments can be accomplished using the teachings of the present invention and that the invention is not limited to the embodiments illustrated for explanatory purposed.

The method according to the present invention may further have a configuration, in which the semiconductor wafer is a silicon wafer. Having such configuration, metal elements existing in vicinity of the surface of the silicon wafer may be analyzed with higher sensitivity in a simple and easy technique.

In the method according to the present invention, the metal element may contain one, two or more element(s) selected from the group consisting of Ti, Fe, In, Ce, Zr, Hf, Y, La, Ru, Pt, Ir, Rh, Pd and Os. Having such configuration, the metal elements, which have been conventionally difficult to be analyzed, may be analyzed with higher sensitivity.

For example, in the method according to the present invention, the metal element may include a platinum group metal element. The platinum group metal elements include metal elements in VIII group to X group in the long periodic table, such as Ru, Rh, Pd, Os, Ir and Pt. Since, in the method according to the present invention, the metal elements on the surface of the wafer may be incorporated in the liquid and then, definitely be aggregated, the platinum group metals, which has been conventionally difficult to be analyzed, may be definitely aggregated on the wafer and definitely analyzed. In other words, even if the metal impurity itself is not dissolved into hydrofluoric acid, the metal impurity is stripped or eliminated from the surface of the semiconductor wafer as the underlying oxide film is dissolved, and then is incorporated into the liquid.

In the method according to the present invention, the analyzing metal element may include analysises of: at least one element selected from a group (i) consisting of Ti, Fe and In; and at least one element selected from a group (ii) consisting of Ce, Zr, Hf, Y, La, Ru, Pt, Ir, Rh, Pd and Os simultaneously.

Having such configuration, both of the elements of group (i), which is soluble to the liquid, and elements of the group (ii), which generate insoluble compounds and/or readily to be firmly adsorbed onto the wafer, may simultaneously be analyzed. Therefore, it may be possible to analyze the metal elements on the surface of the wafer in more simple and easy technique.

In the method according to the present invention, a concentration of the hydrofluoric acid in the liquid may be equal to or greater than 40 wt %. Having such configuration, the metal elements existing on the surface of the wafer may more definitely be incorporated into the liquid. Thus, further accurate analysis may be achieved.

In the method according to the present invention, the drying the liquid in the aggregating the liquid to obtain the aggregated material containing the metal element may include obtaining the aggregated material, which is incorporated within a spot of the X-ray irradiating on the surface of the semiconductor wafer in the analyzing the metal element. Having such configuration, X-ray may definitely be irradiated on the aggregated material to conduct the analysis. Thus, the analysis for the metal elements existing on the surface of the wafer may more definitely be conducted.

In the method according to the present invention, the metal element may be a metal element contained in a metal impurity adhered onto the surface of the semiconductor wafer. Having such configuration, the metal impurity adhered onto the surface of the semiconductor wafer may be analyzed with higher sensitivity.

In the method according to the present invention, the metal impurity may contain a component that is not soluble into the liquid. Having such configuration, the insoluble metal impurities, which are difficult to be analyzed in the conventional chemical analysises, may definitely be analyzed. Further, the analysis may be conducted by concentrating the insoluble metal impurity on the wafer. Thus, a trace amount of metal impurity may be analyzed with higher sensitivity.

Embodiments according to the present invention will be described as follows in reference to the annexed figures. In all figures, identical numeral is assigned to similar element, and the detailed description thereof is not presented.

FIG. 1 is a flow chart, describing a procedure for analyzing metal elements existing on a wafer according to the present embodiment. First, as shown in FIG. 1, high concentration HF solution (hydrofluoric acid) is dropped onto the surface of the wafer (S101). In this occasion, high concentration HF solution is dropped onto a native oxide film having a hydrophilic property, which is formed on the surface of the wafer having a hydrophobic property. By providing the droplets of high concentration HF solution, the native oxide film on the surface of the wafer is dissolved into the solution, and the metal elements or compounds thereof existing in vicinity of the surface of the wafer are eliminated from the wafer and are incorporated into the high concentration HF solution (S102). The forms of the incorporation thereof into the solution are not particularly limited, and may include, for example, solution, dispersion, sedimentation or the like.

When the native oxide film on the surface of the wafer is dissolved into the high concentration HF solution, the surface of the wafer having the hydrophobic property is exposed, and thus the high concentration HF solutions are moved and mutually fused or agglomerated to grow up to the liquid droplets. In this occasion, the droplets of the high concentration HF solution are aggregated at a predetermined position on the surface of the wafer (S103). Then, the metal elements or compounds thereof existing in the high concentration HF are also moved as the droplets are moved to aggregate at the predetermined position on the wafer. Then, the aggregated droplet of the high concentration HF solution is dried (S104). Then, aggregated material of the metal elements or compounds thereof existing in the high concentration HF solution deposits on the surface of the wafer as a drying material. Then, the aggregated material is irradiated with X-ray at an angle for promoting total reflection, and the total reflection X-ray fluorescence spectrometry is conducted to detect the emitted fluorescent X-ray, thereby analyzing the kind and the quantity of the metal elements existing on the surface of the wafer (S105).

FIGS. 2A to FIG. 2C and FIGS. 3A to FIG. 3C are schematic perspective views, illustrating procedures of step 101 to step 104. The procedures of step 101 to step 104 will be specifically described in reference to these figures as follows.

Figure 2B:
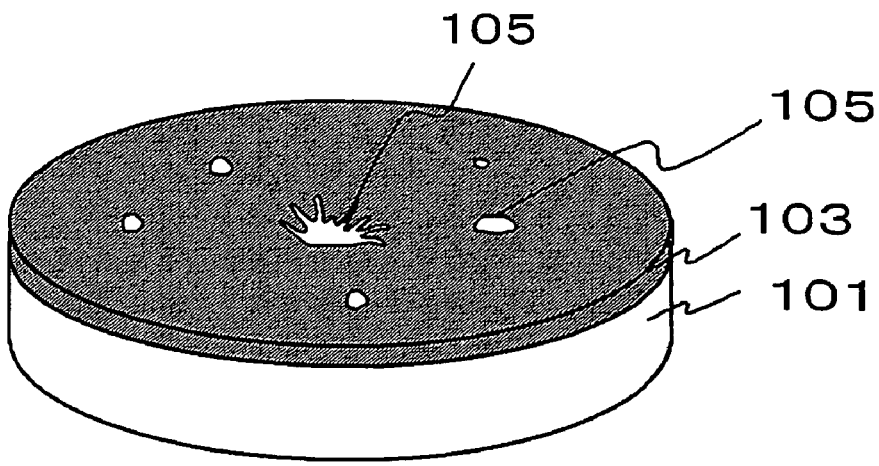
FIG. 2B is a schematic perspective view of a wafer, illustrating a procedure for analyzing the metal element on the wafer according to the embodiment.

In the step 101, a silicon substrate 101 having a native oxide film 103 formed on a surface thereof is employed as a wafer, as shown in FIG. 2A. A high concentration HF solution 105 is dropped onto the surface of the wafer (FIG. 2A). The native oxide film 103 is a $SiO_2$ film, and since the surface thereof has a hydrophilic property, the dropped high concentration HF solution 105 is scattered across the surface of the native oxide film 103 (FIG. 2B).

Figure 2C:
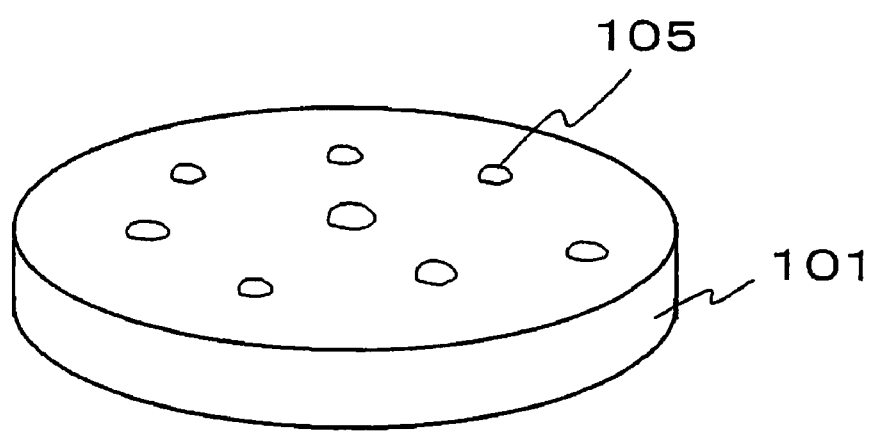
FIG. 2C is a schematic perspective view of a wafer, illustrating a procedure for analyzing the metal element on the wafer according to the embodiment.

In the step 102, the native oxide film 103 is dissolved into the high concentration HF solutions 105 that are dropped in the previous step 101. In this occasion, the native oxide film 103 is dissolved in the high concentration HF solutions 105, and the metal elements or compounds thereof existing in the native oxide film 103 or in vicinity of the surface of the silicon substrate 101 are simultaneously eliminated from the wafer to incorporate them into the liquid droplets (FIG. 2C). Here, the step 101 and the step 102 ordinarily progresses successively.

A liquid solution containing hydrofluoric acid at a concentration of 20 wt % or greater, preferably 40 wt % or greater, is employed as the high concentration HF solution 105. Having such solution, the native oxide film 103 is definitely dissolved, and simultaneously the metal elements existing on the surface of the wafer are eliminated from the silicon substrate 101 and eliminated metal elements are incorporated in the high concentration HF solution droplets 105. Further, the high concentration HF solution 105 may contain peroxides such as $H_2O_2$ and the like or acids except hydrofluoric acid such as $H_2SO_4$ and the like. Further, the concentration of the high concentration HF solution 105 is not limited, and, for example, a HF solution at a concentration of 50 wt %, which has highest concentration among the commercially available products, may be employed.

In addition, the quantity of the high concentration HF solution 105 dropped in the step 101 may be suitably selected corresponding to the line width of X-ray irradiating onto the surface of the silicon substrate 101 in the step 105. For example, the quantity thereof may be selected to a level providing a droplets having a width that is not larger than the line width of X-ray. Having such quantity, further precise analysis of the metal elements can be conducted. Specifically, for example, when the line flux of X-ray is about 10 mm φ, the quantity of the droplet of high concentration HF solution 105 may be 50 µL to 1000 µL. More specifically, the quantity of the droplet of high concentration HF solution 105 may be, for example, 500 µL or the like.

In addition, in the step 102, the silicon substrate 101 may be moved so as to move the relative position of the high concentration HF solution 105 over the silicon substrate 101. Having such procedure, the native oxide film 103 on the entire surface of the silicon substrate 101 can be definitely dissolved.

Figure 3A:
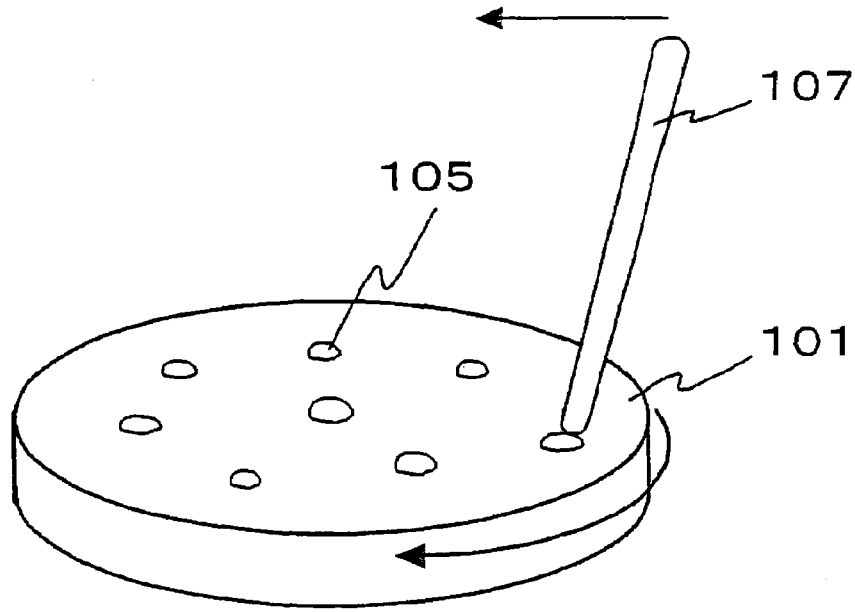
FIG. 3A is a schematic perspective view of a wafer, illustrating a procedure for analyzing the metal element on the wafer according to the embodiment.
Figure 3B:
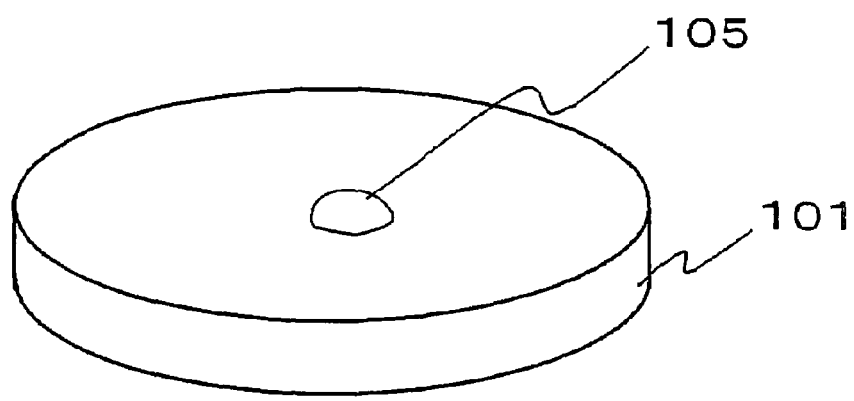
FIG. 3B is a schematic perspective view of a wafer, illustrating a procedure for analyzing the metal element on the wafer according to the embodiment.

In the step 103, the droplets of the high concentration HF solution 105 is recovered at a predetermined position on the silicon substrate 101 and aggregated. The aggregated material of the droplets may be formed in one place on the wafer, or may be aggregated at multiple places on the wafer. In addition, while the recovery method is not particularly limited, the droplets can be moved, for example, by moving a recovery bar 107 with the condition, in which a tip of the recovery bar 107 contacts with the droplet of the high concentration HF solution 105 (FIG. 3A). In this occasion, as shown in FIG. 3A, the recovery bar 107 may be moved from the peripheral portion toward the center portion of the silicon substrate 101 while rotating the silicon substrate 101 around a rotating axis of a normal line of the surface thereof to recover the high concentration HF solution 105 around the center portion of the surface of the silicon substrate 101 (FIG. 3B). The material for composing the recovery bar 107 may be polytetrafluoroethylene (PTFE) or Teflon™, for example.

Figure 3C:
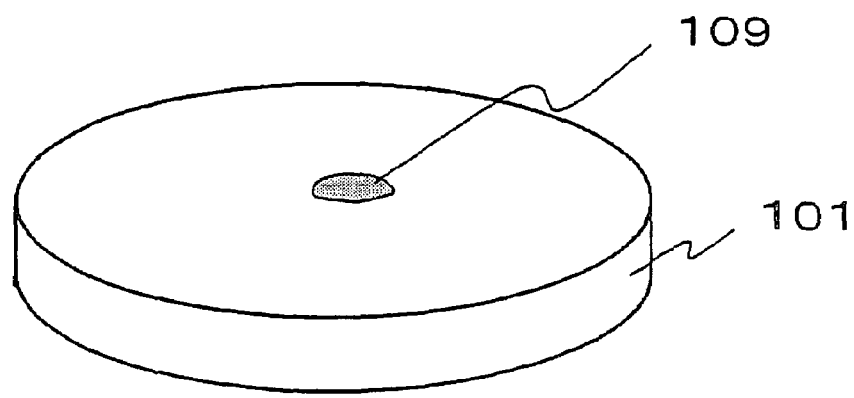
FIG. 3C is a schematic perspective view of a wafer, illustrating a procedure for analyzing the metal element on the wafer according to the embodiment.

In the step 104, the droplets that are recovered on the silicon substrate 101 are dried to deposit the aggregated materials containing metal elements on the surface of the silicon substrate 101 (FIG. 3C). Here, the shape of the aggregated materials are not particularly limited, and, they can be deposited to have a shape such as, for example, particulate form, thin film form, flat plate form or the like. The drying process and drying condition are not particularly limited, and they can be heated and dried at, for example, a temperature within a range of from ambient temperature (20 degree C.) to about 100 degree C. for 1 to 10 minute(s). Further, an evacuating drying may be conducted at the above-described temperature.

Serial steps from the step 101 to the step 104 may be conducted in a clean room or the like. Having such procedure, a generation of a contamination may be inhibited.

In the step 105, a TXRF analysis of the aggregated material 109 is conducted. For example, WLβ ray, AgKα ray, MoKα ray or the like may be employed as the primary X-ray. The irradiating region of the primary X-ray may be, for example, a generally circular region having a diameter of about 10 mm. Further, a detection region of the fluorescent X-ray may be, for example, a generally circular region having a diameter of about 10 mm. Since the metal elements on the wafer are concentrated at a predetermined position to obtain the dried aggregated material 109 in the present embodiment, the aggregated material is irradiated by X-ray to analyze the metal elements on the wafer with higher sensitivity.

Advantageous effects obtainable by the analyzing method according to the present embodiment will be described. In the analyzing method according to the present embodiment, the high concentration HF solution 105 having a concentration of equal to or higher than 20 wt % is dropped onto the surface of the native oxide film 103 formed on the silicon substrate 101 in the step 101 and the step 102. Since the high concentration HF solution 105 is disposed as a liquid form on the native oxide film 103, the native oxide film 103 is definitely dissolved into the liquid and the metal elements existing in the top portion of the native oxide film 103 or in the interior of the native oxide film 103 are eliminated from the wafer to be incorporated into the high concentration HF solution 105. The metal elements or compounds thereof are not necessary to be dissolved in the high concentration HF solution 105, and it is sufficient that the metal elements may just be included or may exist in the high concentration HF solution 105. Thus, the metal elements, which are difficult to be analyzed in the conventional method, can be analyzed. For example, the method is preferably employed for analyzing heavy metal contaminations on the surface of the wafer. This advantageous effect is considerably achieved when HF concentration in the employed high concentration HF solution 105 is equal to or greater than 40 wt %.

In addition, the eliminated metal elements are aggregated in a predetermined position on the wafer in the step 103. Thus, a trace amount of the elements existing on the wafer can also be aggregated in the predetermined position on the wafer. Therefore, TXRF analysis can also definitely be conducted with sufficient measurement sensitivity even for heavy metals having same or larger atomic number than W in the periodic table, which does not provide sufficient sensitivity by the conventional TXRF.

The method of the present embodiment can simultaneously conduct analysises for the various metal elements having various kinds of properties. For example, a sample containing at least every one metal element from each of the following group (a) to group (c) can simultaneously be analyzed by one measurement. In addition, a sample containing a plurality of metal element selected from one of the following group (a) to group (c) can also simultaneously be analyzed by one measurement.

group (a): metal elements such as first row transition metal such as Fe, Ti and the like or metal element such as In and the like;

group (b): metal elements such as Ce and the like; and group (c): metal elements such as the platinum group metals including metal elements in VIII group to X group in the long periodic table, such as Ru, Rh, Pd, Os, Ir and Pt, and elements such as Zr, Hf, Y, La and the like.

Here, the metals of the above-described group (a) are soluble to HF aqueous solution, and these metal elements are difficult for being analyzed due to an interference in the conventional ICPQMS. In addition, the metals of the above-described group (b) react with high concentration HF to form insoluble compounds. For example, in case of Ce, insoluble material of $CeF_3$ or the like is generated. In addition, the elements of the above-described group (c) such as platinum group metals and high-k materials such as Zr, Hf, Y, La and the like generates relatively strong mutual interaction with Si, and thus they adsorbs comparatively firmly to the surface of the silicon substrate 101.

On the other hand, when the conventional chemical analysis is concerned, the analysis of the metal element that is insoluble to a liquid employed in the analysis is difficult. The above-described Japanese Patent Laid-Open No. 1990-28,533 employs the method of dropping a diluted HF containing solution containing about 0.5 to 2 wt % of HF onto the wafer surface to dissolve the metal elements into the HF containing solution, and since the metal elements of the above-described group (b) or group (c) can not be dissolved in this technique, the analysises of these metal elements are difficult. Further, since the metal elements of the above-described group (b) react with high concentration HF solution to generate insoluble compounds, in the ICPQMS, analysis cannot be conducted even in the case of employing the high concentration HF solution. In addition, the metal elements of the above-described group (c) exhibit comparatively strong mutual interaction with Si, and thus when the native oxide film 103 is dissolved, the elements are adhered again to the surface of the silicon substrate 101. Therefore, the analysis thereof is difficult in the case of employing high concentration HF solution. On the contrary, in the method according to the present embodiment, since these insoluble elements/compounds are eliminated from the wafer to inhibit the re-adhesion, the analysis thereof can be carried out on the wafer according to the present embodiment.

In addition, in the case the above-described Japanese Patent Laid-Open No. 1990-28,533, even if the element that is soluble to HF aqueous solution as the above-described group (a) are analyzed, the minimum limit of detection is increased by a molecular interference, and thus it is difficult to simultaneously analyze for a plurality of elements. On the contrary, the method according to the present embodiment allows to simultaneously analyze a plurality of elements by employing TXRF analysis with higher sensitivity. For example, simultaneous analysis of Fe and Ti can be conducted.

In the method described in Japanese Patent Laid-Open No. 2004-28,787, HF vapor having highly concentration is employed to dissolve the native oxide film 103 therein, and these dissolved metal elements are deposited on the surface of the wafer. Then, the TXRF analysis is carried out without moving these metal elements from the original positions. Thus, the analysis is difficult when the existing metal element is in a trace amount. For example, when elements such as Fe, In, Ti and the like are simultaneously analyzed by TXRF, sufficient sensitivity is not obtained in the conventional method. On the contrary, in the method of the present embodiment, high concentration HF solution 105 is employed in the step 102 and the step 103 to eliminate these metal elements and aggregate these metal elements on the predetermined position on the wafer, and thus a trace amount of element can be concentrated by moving thereof to allow conducting the analysis.

While the present invention has been described in reference with the embodiment, it is apparent to those skilled in the art that the disclosures contained herein are for the purpose of illustrating the present invention only, and other various configurations of the structures or processes may be suitably employed without departing from the scope and spirits of the invention.

For example, while the above embodiment is illustrated in reference to the wafer having the native oxide film 103 formed on the surface of the silicon substrate 101, the film formed on the surface of the silicon substrate 101 may be a film other than the native oxide film, provided that the film is capable of being dissolved into the high concentration HF solution 105. For example, the film may be an oxide film other than the native oxide film. Alternatively, the film may be a nitride film such as a native nitride film and the like. Since the metal impurities included within these films are capable of being dissolved into the high concentration HF solution 105 and simultaneously being eliminated from the wafer, the analysis thereof can be definitely conducted.

EXAMPLES

First Example

In this first example, ruthenium (Ru) contained in a liquid dropped onto a wafer was recovered by employing various kinds of etching solutions, and the recovery rate was evaluated by TXRF analysis. A liquid solution containing Ru at a known amount was dropped onto a center portion of a clean silicon wafer, and then dried to obtain a reference sample (sample 1). Also, a liquid solution containing Ru at a known amount was dropped onto a clean silicon wafer to form a dapple pattern and the wafer was dried, and thereafter a HF aqueous solution at a concentration of 30 to 50 wt %. was dropped onto the wafer, and then Ru was recovered in a position in vicinity of the center portion of the wafer, and the wafer was dried again (sample 2). The similar process as the preparation process for sample 2 was conducted except that vapor of HF aqueous solution of 50 wt % was sprayed over the surface of the wafer instead of dropping HF aqueous solution of 30 to 50 wt %, and after an etch was conducted, pure water was dropped on the surface of the wafer and the droplets were aggregated around the center portion of the wafer, and then dried again (sample 3). The similar process as the preparation process for sample 3 was conducted except that nitrohydrochloric acid was dropped onto the wafer in place of pure water, and the dropped nitrohydrochloric acid droplets were aggregated around the center portion of the wafer, and then evaporated and dried again (sample 4). These samples were analyzed by TXRF, and the ratio of the quantity of obtained Ru over the quantity of total Ru dropped on the surface of the wafer was determined as a recovery rate (%).

Table 1 summarizes the above-mentioned experimental conditions and the results of the recovery rates. According to Table 1, it is appeared that higher recovery rate of 84.0% was obtained in the analysis for the sample 2, which was recovered by dropping droplets of HF aqueous solution of 30 wt % onto the wafer. On the contrary, even if higher concentration hydrofluoric acid was employed, the recovery rates were lower when hydrofluoric acid was supplied onto the surface of the wafer as a form of vapor. In sample 3, which involves recovering by using pure water, Ru was remained on the surface of the wafer, and thus it was difficult to fully recover thereof. In addition, in case of sample 4 that used nitrohydrochloric acid for recovery, though it was successful to recover the droplets containing Ru, dried $RuO_4$ has scattered over the wafer when the recovered droplets were dried, and thus it was difficult to obtain the aggregated materials containing Ru as drying materials.

Moreover, highly sensitive analysis for analyzing Ru on the wafer with the minimum limit of detection of about $1 \times 10^8$ to $1 \times 10^9$ atms/cm$^2$ was able to be achieved in the analysis for the sample 2. The measurement sensitivity was considerably improved in comparison with the conventional TXRF with the minimum limit of detection of about $1 \times 10^{10}$ to $1 \times 10^{11}$ atms/cm$^2$, concerning the measurement sensibility for Ru. In the meantime, in the case of analyzing the above-described other platinum group metals such as Pt and the like, similar principle thereof can be utilized similarly as in the case of Ru in this example, the analysis can be conducted by lifting the metal element out from the native oxide film by utilizing the high concentration HF solution, and inhibiting re-adhesion to the silicon substrate. Moreover, in the case of analyzing the elements of the high-k materials such as Zr, Hf, Y and La, which exhibit the relatively strong mutual interactions with Si, these elements are eliminated from the wafer by the similar principle, and the re-adhesion to the silicon substrate is inhibited, therefore the analysis thereof can be conducted.

TABLE 1

| SAMPLE No. | Ru DROPPING | ETCHING CONDITIONS | RECOVERY | DRYING | RECOVERY RATE (%) |
|---|---|---|---|---|---|
| 1 | WAFER CENTER | — | — | GOOD | 100 |
| 2 | DAPPLED | 30 vol % HF aq. sol. | GOOD | GOOD | 84.0 |
| 3 | DAPPLED | 50 vol % HF VAPOR DECOMPOSITION + H$_2$O | NO GOOD (REMAINING | GOOD | 30.1 |

TABLE 1-continued

| SAMPLE No. | Ru DROPPING | ETCHING CONDITIONS | RECOVERY | DRYING | RECOVERY RATE (%) |
|---|---|---|---|---|---|
| 4 | DAPPLED | RECOVERY 50 vol % HF VAPOR DECOMPOSITION + NITROHYDROCHLORIC ACID RECOVERY + EVAPORATION DRYING | ON WAFER) GOOD | NO GOOD (RuO4 SCATTERING) | 40.3 |

Second Example

In this second example, Ce dropped on the wafer was recovered by the method described in the first example. Then, the obtained recovery rates thereof were compared by the difference of the recovery method and the analysis method. A solution containing Ce at a known amount was dropped on the wafer and the wafer was dried, and thereafter, a HF aqueous solution at a concentration of 30 to 50 wt % was dropped onto the wafer, and Ce was recovered in a position in vicinity of the center portion of the wafer, and the wafer was dried again. TXRF analysis of the obtained dried material was conducted (sample 5). Further, the similar process as the preparation process for sample 5 was conducted except that, ICPQMS analysis of the HF aqueous solution, which was recovered in vicinity of the center portion of the wafer, was conducted (sample 6). Moreover, the similar process as the preparation process for sample 5 was conducted except that vapor of HF aqueous solution of 50 wt % was sprayed on the surface of the wafer, and after an etch was conducted, pure water was dropped on the surface of the wafer and the droplets of the water were aggregated around the center portion of the wafer, and then dried again, and finally the resultant product was TXRF analyzed (sample 7).

The results were that, while the recovery rate for the sample 5 was around 90%, the recovery rates for the sample 6 and the sample 7 were lower, and were 17.4% and 25.8%, respectively. Concerning Ce, the high concentration HF aqueous solution of 30 to 50 wt % was dropped on the wafer and the droplets were recovered at a predetermined position on the wafer to incorporate Ce within the HF aqueous solution and the Ce was concentrated. On the contrary, since ICPQMS analysis was conducted in the sample 6, $CeF_3$, which is insoluble to the HF aqueous solution, cannot be analyzed, and the recovery rate thereof was decreased. In addition, in the sample 7, which includes conducting the recovery with pure water, the recovery was difficult similarly as in the case of the above-described sample 3.

Further, high sensitivity analysis for analyzing Ce with minimum limit of detection of about $1 \times 10^8$ to $1 \times 10^9$ atms/$cm^2$ was achieved in the sample 5. Therefore, the measurement sensitivity was considerably improved in comparison with the conventional TXRF with the minimum limit of detection of the measurement sensibility for Ce of about $1 \times 10^{10}$ to $1 \times 10^{11}$ atms/$cm^2$. In the meantime, in the case of analyzing the other metal elements that form the insoluble materials, similar principle thereof can be utilized similarly as in the case of Ce in this example, the analysis can be conducted by lifting the metal elements out from the native oxide film by utilizing the high concentration HF solution, and by aggregating thereof on the wafer.

According to the method of the present invention, it was confirmed that Ce and a platinum group metal were simultaneously analyzed with a level of minimum limit of detection of $1 \times 10^8$ to $1 \times 10^9$ atms/$cm^2$.

Comparative Example

In this comparative example, simultaneous analysises for Ti and Fe by ICPQMS were conducted. A liquid solution containing Fe and Ti at known amounts was dropped onto the wafer to make the following samples for analysis by employing the different recovery methods.

Sample 7: Vapor of HF aqueous solution of 50 wt % was sprayed on the surface of the wafer, and after an etching was conducted, pure water was dropped on the surface of the wafer and the droplets were aggregated around the center portion of the wafer to recover thereof.

Sample 8: Vapor of HF aqueous solution of 50 wt % was sprayed on the surface of the wafer, and after an etch was conducted, an aqueous solution of 1 to 5 wt % of HF and $H_2O_2$ was dropped on the surface of the wafer and the droplets were aggregated around the center portion of the wafer to recover thereof.

Figure 4:
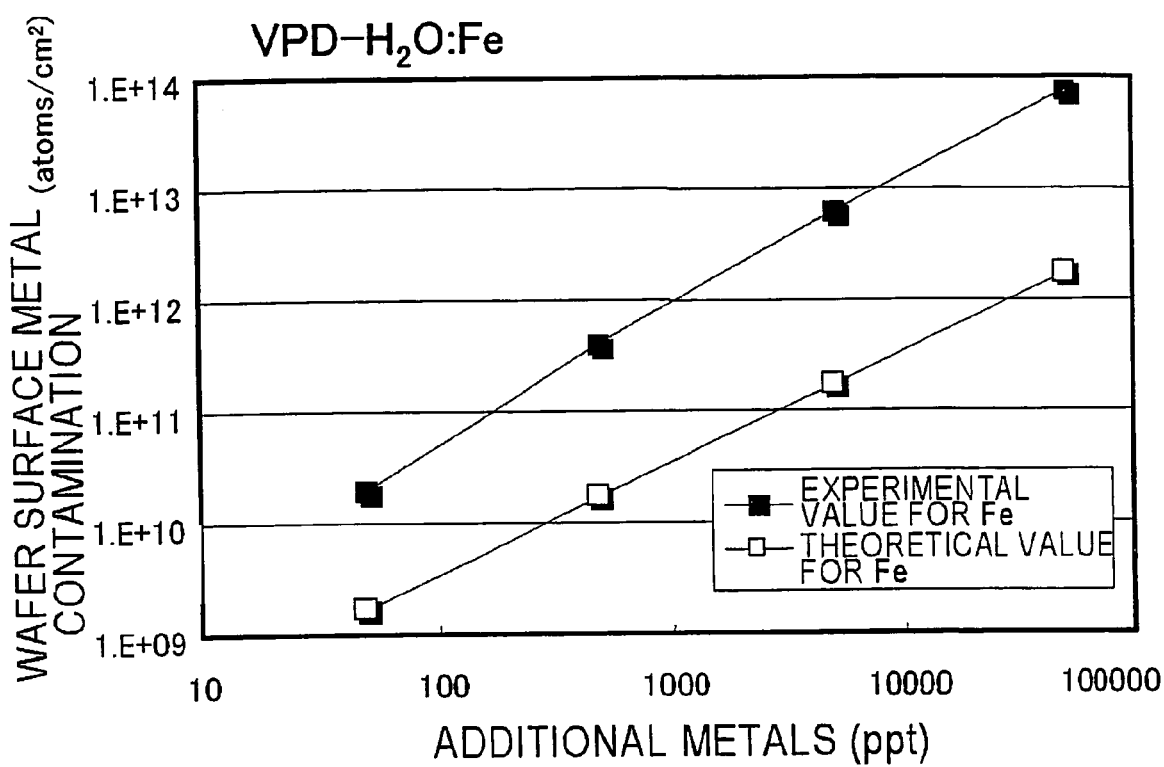
FIG. 4 is a graph, showing an analysis results according to a comparative example.
Figure 5:
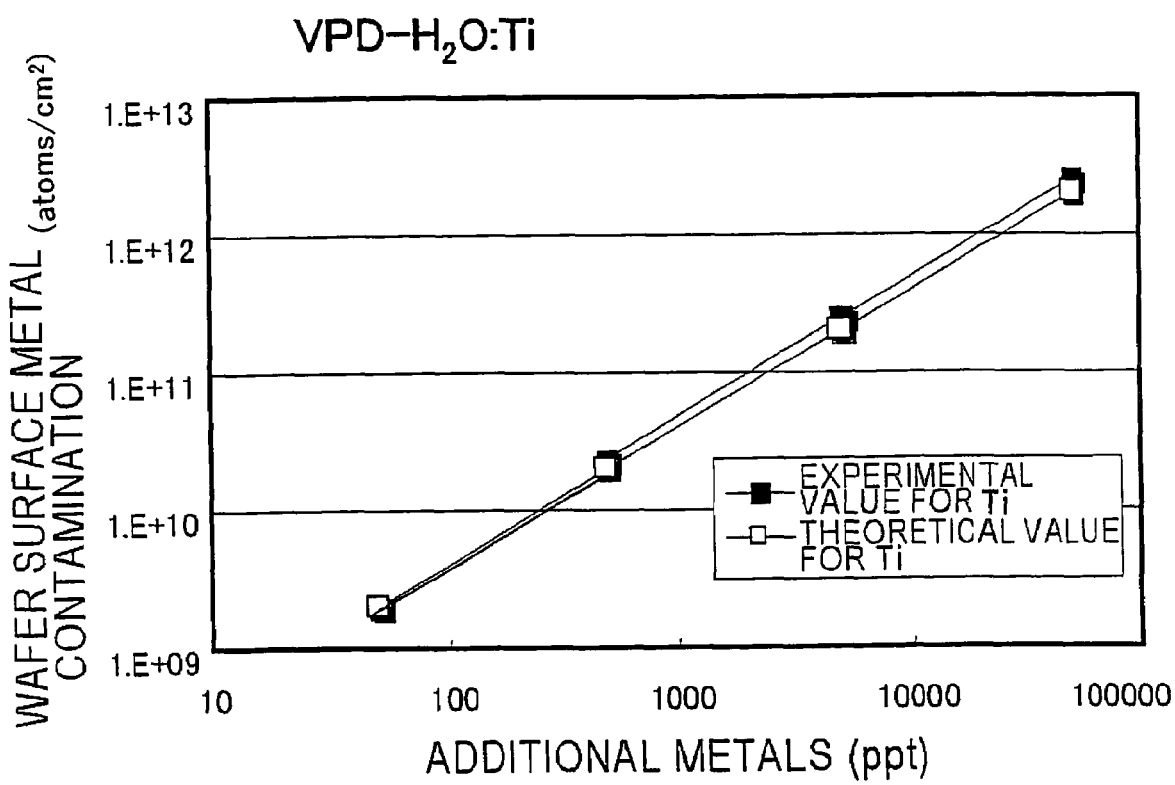
FIG. 5 is a graph, showing an analysis results according to the comparative example.
Figure 6:
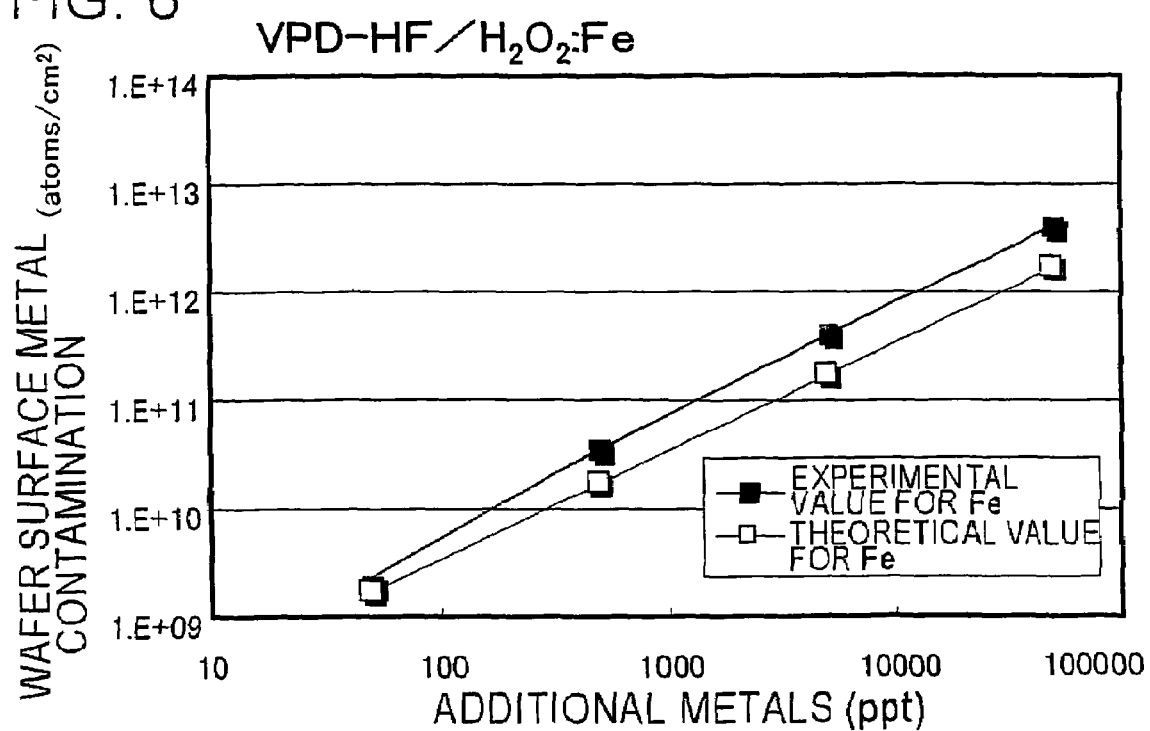
FIG. 6 is a graph, showing an analysis results according to the comparative example.
Figure 7:
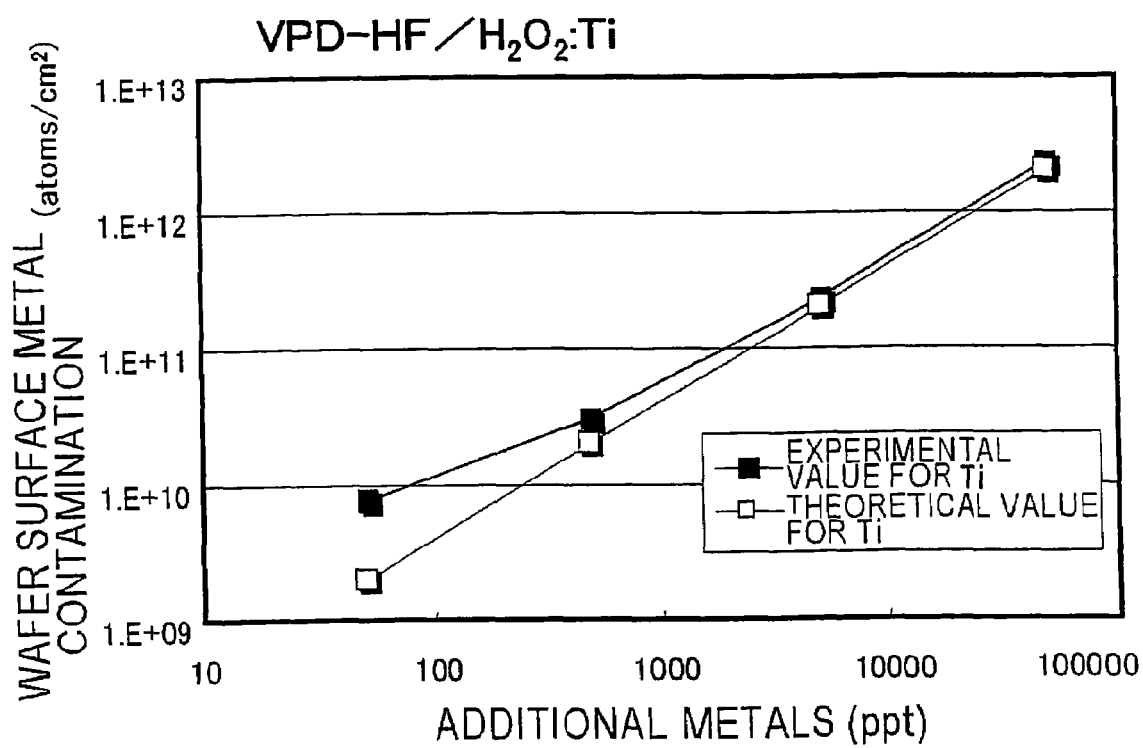
FIG. 7 is a graph, showing an analysis results according to the comparative example.

FIG. 4 to FIG. 7 are graphs showing the ICPQMS measurement results for each of samples that were recovered. FIG. 4 and FIG. 5 show the measurement results of Fe and Ti of the sample 7, respectively. FIG. 6 and FIG. 7 show the measurement results of Fe and Ti of the sample 8, respectively. "VPD" appeared in FIG. 4 to FIG. 7 indicates HF vapor decomposition.

It can be seen from FIG. 4 and FIG. 5 that better measurement results for Ti were obtained by conducting the recovery utilizing pure water, though slight deviations in the measured values were occurred for Fe. It is considered because an interference of Si—Si caused in the dissolution of the native oxide film may affect the results. On the other hand, it can be seen from FIG. 6 and FIG. 7 that better measurement results for Fe were obtained by conducting the recovery utilizing the $HF/H_2O_2$ solution, though the analysis for Ti conducted at lower concentration region was difficult. It is considered because the analysis for Ti was interfered by SiFH generated between Si and HF.

According to the results of the comparative example, it was found that in the conventional method, it is difficult to conduct the simultaneous analysises for both Fe and Ti at higher precision and accuracy. Although the minimum limit of detection for Fe in the conventional TXRF analysis was $5 \times 10^9$ atms/$cm^2$, and the minimum limit of detection for Ti was $5 \times 10^{10}$ atms/$cm^2$, the minimum limit of detection for simultaneous analysis for both Fe and Ti was about $1 \times 10^{11}$ atms/$cm^2$.

On the contrary, the use of the method of the present invention allows to provide an accurate and simultaneous measurements for these elements. For example, the simultaneous measurement for Ti and Fe with minimum limit of detection for both element of about $1 \times 10^9$ atms/$cm^2$ can be provided. In addition, the other metal elements such as In and the like, which are soluble into the HF aqueous solution but difficult in the measurement by ICPQMS due to interferences, can be simultaneously analyzed. Moreover, the other first row transition metals such as Co, Cu and the like, which are soluble into the HF aqueous solution, can also be analyzed simultaneously with the analysis for these metal elements and/or other metal elements with higher sensitivity.

It is apparent that the present invention is not limited to the above embodiment, that may be modified and changed without departing from the scope and spirit of the invention.

What is claimed is:

1. A method for analyzing a metal element, comprising:
   dropping a liquid on a surface of a semiconductor wafer having an oxide film formed thereon to dissolve said oxide film in said liquid, thereby incorporating a metal element contained in said semiconductor wafer into said liquid, said liquid containing hydrofluoric acid at a concentration of equal to or greater than 20 wt %;
   aggregating said liquid incorporating said metal element on said semiconductor wafer;
   drying said aggregated liquid to obtain an aggregated material containing said metal element on said semiconductor wafer; and
   analyzing said metal element by detecting fluorescent X-ray emitted from said semiconductor wafer, said fluorescent X-ray being emitted by irradiating X-ray upon said semiconductor wafer at an incident angle of providing a total reflection thereof.

2. The method according to claim 1, wherein said semiconductor wafer is a silicon wafer.

3. The method according to claim 1, wherein said metal element contains one, two or more element(s) selected from the group consisting of Ti, Fe, In, Ce, Zr, Hf, Y, La, Ru, Pt, Ir, Rh, Pd and Os.

4. The method according to claim 1, wherein said analyzing said metal element includes analyses of:
   at least one element selected from a group (i) consisting of Ti, Fe and In; and
   at least one element selected from a group (ii) consisting of Ce, Zr, Hf, Y, La, Ru, Pt, Ir, Rh, Pd and Os simultaneously.

5. The method according to claim 1, wherein the concentration of said hydrofluoric acid in said liquid is equal to or greater than 40 wt %.

6. The method according to claim 1, wherein said aggregated material containing said metal element is incorporated within a spot of said X-ray irradiating on the surface of said semiconductor wafer.

7. The method according to claim 1, wherein said metal element is a metal element contained in a metal impurity adhered onto the surface of said semiconductor wafer.

8. The method according to claim 7, wherein said metal impurity contains a component that is not soluble into said liquid.

9. The method according to claim 1, wherein said liquid contains $H_2O_2$.

10. The method according to claim 1, wherein a line flux of the x-ray is about 10 mm $\phi$, and a volume of the liquid is from 50 µL to 1000 µL.

11. The method according to claim 1, wherein said aggregating is performed with recovery bar.

12. The method according to claim 11, wherein said recovery bar comprises polytetrafluoroethylene.

13. The method of claim 11, wherein the recovery bar moves from a peripheral portion toward a center portion of the semiconductor wafer while rotating the semiconductor wafer.

14. The method according to claim 1, wherein said drying is performed at about 100° C. for 1 to 10 minutes.

15. The method according to claim 1, wherein the irradiating X-ray is a $WL\beta$ ray, a $AgK\alpha$ ray or a $MoK\alpha$ ray.

* * * * *